(12) United States Patent
Otoyo et al.

(10) Patent No.: US 9,200,309 B2
(45) Date of Patent: Dec. 1, 2015

(54) METHOD FOR SCREENING FOR S1P LYASE INHIBITORS USING CULTURED CELLS

(75) Inventors: Mamoru Otoyo, Tokyo (JP); Masakazu Tamura, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/805,787

(22) PCT Filed: Jun. 24, 2011

(86) PCT No.: PCT/JP2011/064535
§ 371 (c)(1),
(2), (4) Date: Dec. 20, 2012

(87) PCT Pub. No.: WO2012/002274
PCT Pub. Date: Jan. 5, 2012

(65) Prior Publication Data
US 2013/0102008 A1    Apr. 25, 2013

(30) Foreign Application Priority Data

Jun. 28, 2010 (JP) ................................. 2010-145754

(51) Int. Cl.
| C12Q 1/02 | (2006.01) |
| C12Q 1/527 | (2006.01) |
| G01N 33/18 | (2006.01) |
| G01N 33/50 | (2006.01) |
| G01N 33/00 | (2006.01) |

(52) U.S. Cl.
CPC ................ *C12Q 1/025* (2013.01); *C12Q 1/527* (2013.01); *G01N 33/1826* (2013.01); *G01N 33/5008* (2013.01); *G01N 33/18* (2013.01); *G01N 2333/968* (2013.01)

(58) Field of Classification Search
None
See application file for complete search history.

(56) References Cited

U.S. PATENT DOCUMENTS

| 7,649,098 | B2 | 1/2010 | Augeri et al. | |
| 8,404,732 | B2 * | 3/2013 | Augeri et al. | 514/397 |
| 8,653,126 | B2 | 2/2014 | Machinaga et al. | |
| 2002/0042091 | A1 * | 4/2002 | Normant et al. | 435/15 |
| 2009/0298901 | A1 | 12/2009 | Wu et al. | |
| 2009/0318516 | A1 | 12/2009 | Burgoon et al. | |
| 2012/0316170 | A1 | 12/2012 | Machinaga et al. | |

FOREIGN PATENT DOCUMENTS

| JP | 2001-518303 A | 10/2001 |
| JP | 2004-509638 A | 4/2004 |
| JP | 2005-531285 A | 10/2005 |
| JP | 2008-530135 A | 8/2008 |
| JP | 2009-527564 A | 7/2009 |
| WO | WO 84/03441 A1 | 9/1984 |
| WO | WO 97/46543 A1 | 12/1997 |
| WO | WO 99/16888 | 4/1999 |
| WO | WO 02/27318 A1 | 4/2002 |
| WO | WO 03/062390 A2 | 7/2003 |
| WO | WO 2006/088944 A1 | 8/2006 |
| WO | WO 2007/100617 A2 | 9/2007 |
| WO | WO 2008/109314 A1 | 9/2008 |
| WO | WO 2008/128045 A1 | 10/2008 |
| WO | WO 2011/102404 A1 | 8/2011 |

OTHER PUBLICATIONS

Melendez, Sphingosine kinase signalling in immune cells: Potential as novel therapeutic target, BBA, 1784: 66-75, 2008.*
Veldhoven et al., Sphinganine 1-phosphate metabolism in cultured skin fibroblasts, Biochem. Journal, 299, 597-601, 1994.*
Desai et al., Fumonisins and fumonisin analogs as inhibitors of ceramide synthase and inducers of apoptosis, BBA, 1585: 188-192, 2002.*
Ohtoyo et al., Sphingosine 1-phosphate lyase inhibition by THI under conditions of vitamin B6 deficiency, Mol. Cell Biochem., Nov. 19, 2014.*
Bandhuvula et al., "A rapid fluorescence assay for sphingosine-l-phosphate lyase enzyme activity," *Journal of Lipid Research*, vol. 48, pp. 2769-2778 (2007).
Bandhuvula et al., "Sphingosine 1-phosphate lyase enzyme assay using a BODIPY-labeled substrate," *Biochemical and Biophysical Research Communications*, vol. 380, pp. 366-370 (2009).
Bedia et al., "Synthesis of a Fluorogenic Analogue of Sphingosine-1-Phosphate and Its Use to Determine Sphingosine-1-Phosphate Lyase Activity," *Chembiochem*, vol. 10, pp. 820-822 (2009).
Edsall et al., "Enzymatic Measurement of Sphingosine 1-Phosphate," *Analytical Biochemistry*, vol. 272, pp. 80-86 (1999).
Kim et al., "Elevation of Sphingoid Base 1-Phosphate as a Potential Contributor to Hepatotoxicity in Fumonisin $B_1$-Exposed Mice," *Arch. Pharm. Res.*, vol. 30, No. 8, pp. 962-969 (2007).

(Continued)

*Primary Examiner* — Taeyoon Kim
*Assistant Examiner* — Srikanth Patury
(74) *Attorney, Agent, or Firm* — Dorsey and Whitney LLP

(57) ABSTRACT

To provide a method for screening using cultured cells, intended to find a compound which increases the amount of sphingosine-1-phosphate or dihydrosphingosine-1-phosphate by SPL inhibitory activity rapidly, simply and highly sensitively. Provided are: a rapid and simple measurement method employing a scintillation proximity assay (SPA); a method with greatly improved detection sensitivity to the activity of a compound by controlling the concentration of the vitamin $B_6$ group in a culture medium to be used in assaying; and others.

13 Claims, 6 Drawing Sheets

(56) References Cited

OTHER PUBLICATIONS

Kumar et al., "Lyase to live by: Sphingosine phosphate lyase as a therapeutic target," *Expert Opin. Ther. Targets*, vol. 13, No. 8, pp. 1013-1025 (2009).

Le Stunff et al., "Role of Sphingosine-1-phosphate Phosphatase 1 in Epidermal Growth Factor-induced Chemotaxis," *The Journal of Biological Chemistry*, vol. 279, No. 33, pp. 34290-34297 (2004).

Lee et al., "A novel method to quantify sphingosine 1-phosphate by immobilized metal affinity chromatography (IMAC)," *Prostaglandins & other Lipid Mediators*, vol. 84, pp. 154-162 (2007).

Murata et al., "Quantitative Measurement of Sphingosine 1-Phosphate by Radioreceptor-Binding Assay," *Analytical Biochemistry*, vol. 282, pp. 115-120 (2000).

Reiss et al., "Sphingosine-phosphate Lyase Enhances Stress-induced Ceramide Generation and Apoptosis," *The Journal of Biological Chemistry*, vol. 279, No. 2, pp. 1281-1290 (2004).

Schwab et al., "Lymphocyte Sequestration Through S1P Lyase Inhibition and Disruption of S1P Gradients," *Science*, vol. 309, pp. 1735-1739 (2005).

Serra et al., "Sphingosine 1-phosphate lyase, a key regulator of sphingosine 1-phosphate signaling and function," *Advances in Enzyme Regulation*, vol. 50, pp. 349-362 (2010).

Vogel et al., "Incomplete Inhibition of Sphingosine 1-Phosphate Lyase Modulates Immune System Function yet Prevents Early Lethality and Non-Lymphoid Lesions," *PLoS ONE*, vol. 4, Issue 1, e4112, 15 pages (2009).

Yatomi et al., "Quantitative Measurement of Sphingosine 1-Phosphate in Biological Samples by Acylation with Radioactive Acetic Anhydride," *Analytical Biochemistry*, vol. 230, pp. 315-320 (1995).

Bagdanoff et al., "Inhibition of Sphingosine-1-Phosphate Lyase for the Treatment of Autoimmune Disorders," *J. Med. Chem.*, 52:3941-3953 (2009).

Bagdanoff et al., Inhibition of Sphingosine 1-Phosphate Lyase for the Treatment of Rheumatoid Arthritis: Discovery of (*E*)-1-(4-((1*R*,2*S*,3*R*)-1,2,3,4-Tetrahydroxybutyl)-1*H*-imidazol-2-yl)ethanone Oxime (LX2931) and (1*R*,2*S*,3*R*)-1-(2-(Isoxazol-3-yl)-1*H*-imidazol-4-yl)butane-1,2,3,4-tetraol (LX2932), J. Med. Chem., 53:8650-8662 (2010).

Gilenya® Product Data Sheet, Novartis Pharmaceuticals Corp., East Hanover, New Jersey, USA, 2012, 17 pages.

Mandala et al., "Alteration of Lymphocyte Trafficking by Sphingosine-1-Phosphate Receptor Agonists," *Science*, 296:346-349 (2002).

Yu et al., "Pharmacokinetic/pharmacodynamic modelling of 2-acetyl-4(5)-tetrahydroxybutyl imidazole-induced peripheral lymphocyte sequestration through increasing lymphoid sphingosine 1-phosphate," *Xenobiotica*, 40(5):350-356 (2010).

English translation of International Search Report issued on Mar. 29, 2011, in PCT Application No. PCT/JP2011/053336, 3 pages.

English translation of International Search Report issued on Sep. 13, 2011, in PCT Application No. PCT/JP2011/064535, 2 pages.

English translation of International Search Report issued on Sep. 4, 2012, in PCT Application No. PCT/JP2012/066357, 4 pages.

Non-Final Office Action mailed May 17, 2013, U.S. Appl. No. 13/579,791, 18 pages.

Response to Non-Final Office Action filed Sep. 3, 2013, U.S. Appl. No. 13/579,791, 12 pages.

Notice of Allowance mailed Oct. 11, 2013, U.S. Appl. No. 13/579,791, 11 pages.

Bushey et al., "Intramolecular Nitrogen-Phosphorus Interactions of Phosphate Esters," J. Org. Chem., (1985), 50:2091-2095.

European Supplementary Search Report issued on Feb. 3, 2015, in European Patent Application No. 12 80 4846, 7 pages.

\* cited by examiner

METHOD FOR SCREENING FOR S1P LYASE INHIBITORS USING CULTURED CELLS

This application is a national stage application under 35 U.S.C. §371 of International Application No. PCT/JP2011/064535, filed Jun. 24, 2011, entitled "Method for Screening for S1P Lyase Inhibitor Using Cultured Cell," which claims priority to Japanese Patent Application No. 2010-145754, filed Jun. 28, 2010, the contents of all of which are hereby incorporated in their entirety by reference.

TECHNICAL FIELD

The present invention relates to a method for high-speed multiple sample screening for an S1P lyase inhibitor useful as a novel immunosuppressive agent based on an activity of decreasing the number of lymphocytes in the circulating blood.

BACKGROUND ART

It is known that sphingosine-1-phosphate (hereinafter referred to as "S1P") is a bioactive lipid that regulates cell proliferation, survival and migration and plays an important role in angiogenesis and lymphocyte migration (see, for example, Non-Patent Document 1). The concentration of S1P in the circulating blood and tissues is tightly regulated by a plurality of enzymes, and particularly, S1P lyase (hereinafter referred to as "SPL") which is an enzyme irreversibly cleaving S1P. SPL is considered to be an essential factor for forming an S1P concentration gradient between blood and lymphoid tissues necessary for circulation of lymphocytes. In fact, in an analysis using SPL knockout mice, not only a dramatic increase in the concentration of S1P in lymphoid tissues, but also a significant decrease in the number of lymphocytes in the circulating blood is observed (see, for example, Non-Patent Document 2). Further, it is reported that 2-acetyl-4-tetrahydroxybutylimidazole (hereinafter referred to as "THI") which has the activity of decreasing the number of lymphocytes in the peripheral blood inhibits the formation of an S1P concentration gradient by decreasing the SPL activity in lymphoid tissues in vivo (see, for example, Non-Patent Document 3). From these findings, it is expected that an SPL inhibitor may be used as a novel immunosuppressive agent based on the activity of decreasing the number of lymphocytes in the circulating blood for the avoidance of transplant rejection or various autoimmune diseases.

As for screening for an SPL inhibitor, several assay methods using SPL enzymatic activity in a cell-free system as an index have been reported (see, for example, Non-Patent Documents 4 to 6). However, an inhibitor specific to SPL has not been reported so far. Also for the above-described THI, although THI exhibits SPL inhibitory activity in vivo, the in vitro activity thereof has not been confirmed. On the other hand, it has been known that the accumulation of intracellular S1P is induced by inhibiting SPL. However, there have been no examples of cell-based screening using this accumulation as an index. Several methods for measuring the amount of intracellular S1P are already known (see, for example, Non-Patent Documents 7 to 10). However, all of the methods require a complicated lipid extraction operation, and their low sample processing capability is considered to be a problem. Further, as for the above-described THI, its activity has not also been confirmed in an experimental system using cultured cells. It is considered that this is because the existing experimental conditions are not optimized, and therefore, its activity cannot be detected.

PRIOR ART DOCUMENTS

Patent Documents

Non-Patent Document 1: Expert Opin. Ther. Targets. 2009; 13(8): 1013-1025
Non-Patent Document 2: PLoS One. 2009; 4(1): e4112
Non-Patent Document 3: Science. 2005; 309(5741): 1735-1739
Non-Patent Document 4: J. Lipid Res. 2007; 48(12): 2769-2778
Non-Patent Document 5: Biochem. Biophys. Res. Commun. 2009; 380(2): 366-370
Non-Patent Document 6: Chembiochem. 2009; 10(5): 820-822
Non-Patent Document 7: Anal. Biochem. 1995; 230: 315-320
Non-Patent Document 8: Anal. Biochem. 1999; 272: 80-86
Non-Patent Document 9: Anal. Biochem. 2000; 282: 115-120
Non-Patent Document 10: Prostaglandins & Other Lipid Mediators. 2007; 84: 154-162

SUMMARY OF THE INVENTION

Problems that the Invention is to Solve

An object of the present invention is to provide a method for screening using cultured cells, intended to find a compound which increases the amount of S1P or dihydrosphingosine-1-phosphate (hereinafter referred to as "dhS1P") by direct or indirect SPL inhibitory activity rapidly, simply and highly sensitively.

Means for Solving the Problems

The present inventors have found a method for rapidly and simply measuring the activity of a test compound in increasing the amount of intracellular S1P by using S1P or dhS1P labeled with a radioisotope such as tritium ($^3$H) in a scintillation proximity assay (SPA) and have also found that the detection sensitivity to the SPL inhibitory activity of a test compound can be greatly improved by controlling the concentration of the vitamin $B_6$ group in the culture medium used in the assay, and have thus completed the present invention. An assay method for a sphingosine kinase inhibitor in a cell-free system based on the above SPA has been known (WO 02/027318). However, the method does not measure the amount of S1P by allowing a compound to act on cultured cells as described in the present invention, nor does the method show the improvement of the detection sensitivity to the SPL inhibitory activity of a test compound. Meanwhile, it is known that the in vivo effect of THI is attenuated by administering the vitamin $B_6$ group (Science, 2005; 309(5741): 1735-1739). However, it had not been confirmed that the detection sensitivity to the SPL inhibitory activity of THI or the like can be improved by removing the vitamin $B_6$ group in vitro. The improvement of such detection sensitivity was achieved for the first time by using the assay method described in the present invention.

That is, the present invention includes the following inventions.

(1) A method for identifying, selecting or testing a compound which inhibits the activity of sphingosine-1-phosphate lyase, comprising: (i) a step of seeding cells which express sphingosine-1-phosphate lyase and culturing the cells; (ii) a step of mixing the cells with a labeled lipid substrate and a test compound and culturing the cells; (iii) a step of lysing the cells or a step of separating the culture supernatant from the cells; (iv) a step of bringing a support material which binds to a phosphorylated lipid but does not bind to an unphosphorylated lipid into contact with the cell lysate or the culture supernatant in (iii); (v) a step of measuring the amount of the phosphorylated lipid bound to the support material; and (vi) a step of determining whether the activity of sphingosine-1-phosphate lyase is inhibited using an increase in the amount of the phosphorylated lipid as compared with the case where the test compound is absent as an index.

(2) The method described in (1), characterized in that the lipid substrate is sphingosine or dihydrosphingosine.

(3) The method described in (1) or (2), characterized in that in step (i) and/or (ii), the cells are cultured using a culture medium in which the concentration of the vitamin $B_6$ group is lower than that in a normal culture medium.

(4) The method described in (3), characterized in that the concentration of the vitamin $B_6$ group is 20 µM or less.

(5) The method described in (3), characterized in that the concentration of the vitamin $B_6$ group is 1 µM or less.

(6) The method described in (3), characterized in that the concentration of the vitamin $B_6$ group is 100 nM or less.

(7) The method described in (3), characterized in that the cells are washed with a culture medium which does not contain the vitamin $B_6$ group before the test compound is added, and in step (ii), the culture medium substantially does not contain the vitamin $B_6$ group.

(8) The method described in any one of (1) to (7), characterized in that the support material comprises SPA beads.

(9) The method described in (8), characterized in that the SPA beads are RNA-binding yttrium silicate SPA beads.

(10) The method described in any one of (1) to (9), characterized in that in step (i) and/or (ii), a ceramide synthase inhibitor is added.

(11) The method described in (10), characterized in that the ceramide synthase inhibitor is fumonisin B1.

(12) The method described in any one of (1) to (11), which is for identifying, selecting or testing a compound for preventing or treating an inflammatory bowel disease, an autoimmune disease, multiple sclerosis or an allergic disease.

(13) The method described in (12), wherein the inflammatory bowel disease is ulcerative colitis or Crohn's disease.

(14) The method described in (12), wherein the autoimmune disease is rheumatoid arthritis, systemic lupus erythematosus, antiphospholipid antibody syndrome, multiple myositis, dermatomyositis, systemic scleroderma, Sjogren's syndrome, polyarteritis nodosa, microscopic polyarteritis, allergic granulomatous angiitis, Wegener's granulomatosis or a mixed connective tissue disease.

(15) The method described in (12), wherein the allergic disease is atopic dermatitis, allergic rhinitis, pollinosis, allergic conjunctivitis, allergic gastroenteritis, bronchial asthma, infantile asthma, food allergy, drug allergy or urticaria.

Advantage of the Invention

By the method for screening of the present invention, it becomes possible to find a compound which increases the amount of S1P or dhS1P by its SPL inhibitory activity rapidly, simply and highly sensitively.

BRIEF DESCRIPTION OF THE DRAWINGS

FIG. 2(1) shows the total radioactivity; FIG. 2(2) shows radioactivity by alkaline chloroform extraction; and FIG. 2(3) shows radioactivity measured using SPA beads.

FIG. 3(1) shows the change in SPL mRNA expression level from siRNA transfection; FIG. 3(2) shows the change in SPL activity in an IT-79MTNC3 cell lysate from siRNA transfection; and FIG. 3(3) shows the accumulation of $^3$H-dhS1P in IT-79MTNC3 cells from siRNA transfection. The measurement results in each graph represent data obtained when cells transfected with a negative control siRNA were cultured for 24 hours; data obtained when cells transfected with s73643 were cultured for 24 hours; data obtained when cells transfected with s73644 were cultured for 24 hours; data obtained when cells transfected with s73645 were cultured for 24 hours; data obtained when cells transfected with a negative control siRNA were cultured for 48 hours; data obtained when cells transfected with s73643 were cultured for 48 hours; data obtained when cells transfected with s73644 were cultured for 48 hours; and data obtained when cells transfected with s73645 were cultured for 48 hours, respectively from the left of the graph.

FIG. 4(1) shows the results of an assay using SPA beads; FIG. 4(2) shows the measurement results of the amount of intracellular S1P by LC-MS; and FIG. 4(3) shows the measurement results of the SPL activity in a cell lysate. The concentrations of DOP in each graph are 0 µM, 1.6 µM, 8 µM, 40 µM, 200 µM and 1000 µM, respectively, from the left of the graph.

FIG. 5(1) shows the results of an assay using SPA beads; FIG. 5(2) shows the results of measuring the amount of intracellular S1P by LC-MS; and FIG. 5(3) shows the results of measuring SPL activity in a cell lysate. The concentrations of DOP or THI in FIG. 5(1) are no addition, 1 nM, 10 nM, 100 nM, 1 µM, 10 µM, 100 µM and 1 mM, respectively, from the left of the graph. The concentrations of DOP in each of FIGS. 5(2) and 5(3) are no addition, 1 nM, 10 nM, 100 nM, 1 µM and 10 µM, respectively, from the left of the graph. The concentrations of THI in each of FIGS. 5(2) and 5(3) are no addition, 100 nM, 1 µM, 10 µM, 100 µM and 1 mM, respectively, from the left of the graph.

MODE FOR CARRYING OUT THE INVENTION

1. Construction of Novel SPL Activity Measurement System

Figure 1:
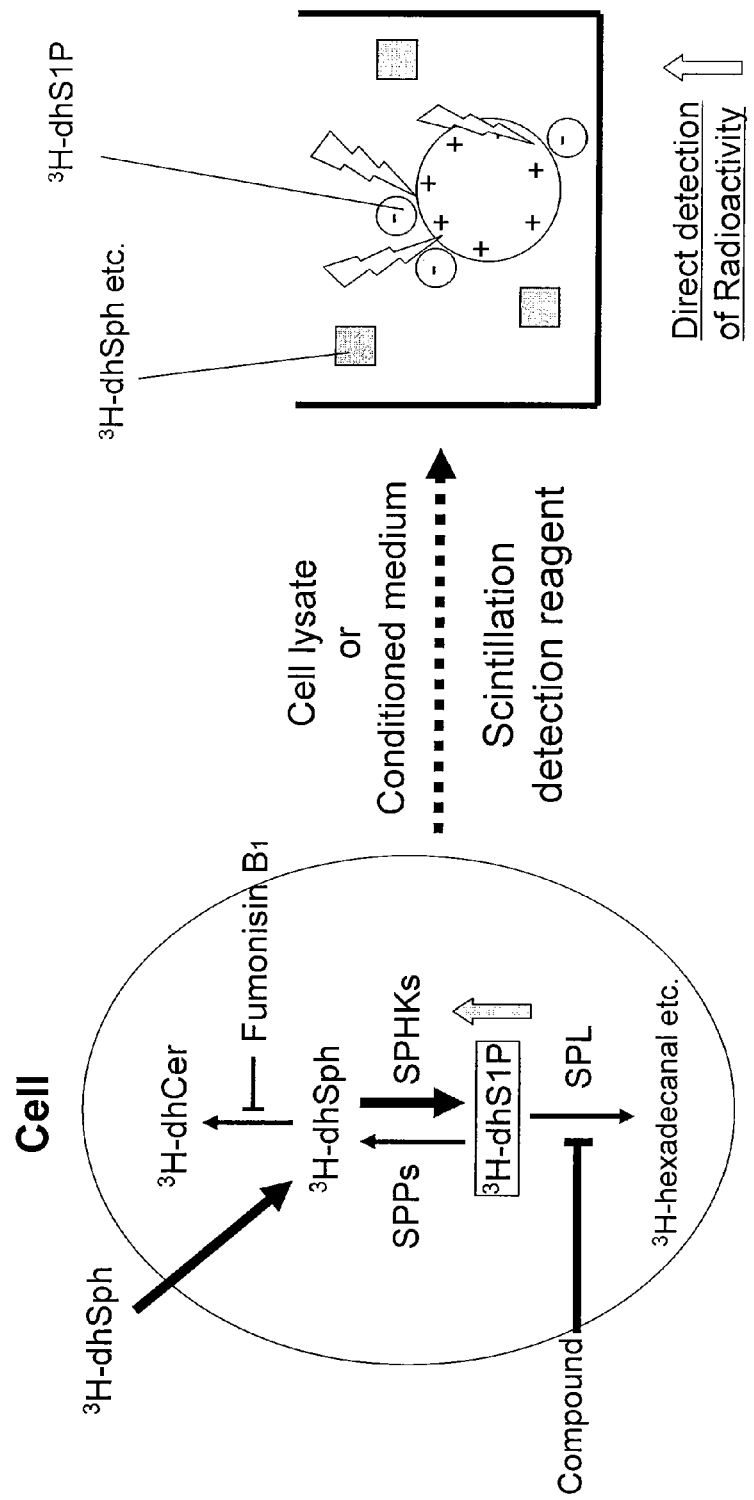
FIG. 1 is a schematic diagram showing the principle of a method for screening of the present invention.

The principle of a newly constructed method for screening is shown in FIG. 1. The method for screening as used herein means a method for identifying, selecting or testing a compound which inhibits the activity of sphingosine-1-phosphate lyase. After a labeled lipid substrate, for example, $^3$H-labeled sphingosine ($^3$H-Sph) or $^3$H-labeled dihydrosphingosine ($^3$H-dhSph) is added to cultured cells to incorporate the lipid into the cells, the lipid is converted into a phosphorylated lipid, for example, $^3$H-labeled S1P ($^3$H-S1P) or $^3$H-labeled dhS1P ($^3$H-dhS1P) by a sphingosine kinase (SPHK) which is endogenously expressed or forcedly expressed. Such a phosphorylated lipid is promptly subjected to irreversible cleavage by SPL or dephosphorylation by a S1P phosphatase (SPP). However, at this time, by inhibiting the SPL activity, the degradation rate is decreased and the phosphorylated lipid accumulates in the cells. That is, if the accumulated amount of $^3$H-S1P or $^3$H-dhS1P in the cells increases when a test compound is added as compared with the case when the test compound is not added, it can be determined that the test compound has SPL inhibitory activity. It is disclosed that in a certain cell line, S1P or dhS1P produced in the cells is secreted outside the cells (Proc. Natl. Acad. Sci. USA. 2006; 103 (44): 16394-16399), and therefore, it is considered that part of $^3$H-S1P or $^3$H-dhS1P accumulated in the cells is secreted outside the cells. Accordingly, if the amount of $^3$H-S1P or $^3$H-dhS1P in the culture supernatant increases, it can be determined that the test compound has SPL inhibitory activity in the same manner. At this time, by performing a treatment with a ceramide synthase inhibitor (such as fumonisin B1) or an inhibitor of SPPs, the improvement of the signal/background ratio or the improvement of the probability of acquisition of a compound specific to SPL can be expected. Further, by knocking out or knocking down an S1P phosphatase gene or a ceramide synthase gene, the same effect can also be expected. Examples of the S1P phosphatase gene include S1P phosphatase-1 and S1P phosphatase-2, and examples of the ceramide synthase gene include LAG1 homolog, ceramide synthase 1 to 6.

As the cultured cells to be used in the present invention, cells such as IT-79MTNC3 cells which are a mouse thymic epithelial cell line can be appropriately selected using the expression of an SPL protein as an index. Further, it is also possible to use cells obtained by introducing an expression vector with an SPL gene integrated thereinto into cultured cells such as 293 cells, CHO cells, NIH-3T3 cells, or COS7 cells. As a gene to be used as the SPL gene, a human SPL gene registered in GenBank with the accession number: NM 003901, a mouse SPL gene registered in GenBank with the accession number: NM_009163, or a rat SPL gene registered in GenBank with the accession number: NM_173116 can be exemplified, however, the gene is not limited to the above described gene group as long as it is a gene encoding a protein having SPL activity.

The radioactivity of $^3$H-S1P or $^3$H-dhS1P accumulated in the cells is measured by lysing the cells using an appropriate solution, mixing the resulting cell lysate with a scintillation reagent serving as a support (such as RNA Binding YSi SPA Scintillation Beads, PerkinElmer) and detecting the radioactivity using a scintillation counter. Further, it is possible to measure the radioactivity of $^3$H-S1P or $^3$H-dhS1P in the culture supernatant by adding the above-described support to the culture supernatant. By doing this, the radioactivity of $^3$H-S1P or $^3$H-dhS1P, only, can be selectively detected without being affected by $^3$H-Sph or $^3$H-dhSph coexisting in the cell lysate or the culture supernatant or by various degradation products generated by an SPL reaction. By using this method, the amount of $^3$H-S1P or $^3$H-dhS1P accumulated in the cells or secreted into the culture supernatant can be simply and promptly measured without resort to an extraction operation using an organic solvent, and as compared with conventional methods which need a lipid extraction operation, the sample processing capability is markedly improved.

Examples of common properties of a solution to be used for lysing the cells in the present invention include the property of having an ability to lyse the cells and the property of not interfering with the binding between the support and $^3$H-S1P or $^3$H-dhS1P (and scintillation luminescence). Accordingly, the above solution is required to contain a surfactant such as Triton or Nonidet. In the Examples in this description, a mixture of commercially available buffers is used as the buffer for lysing the cells, however, the usable solution is not limited thereto. It has been confirmed that a phosphorylated labeled lipid accumulated in the cells can be measured by the method of the present invention also in the case of using, for example, a home-made buffer containing 50 mM Tris-HCl (pH 7.5), 1 mM $Na_3VO_4$, 1 mM NaF, 0.1% BSA, 1% Triton X-100, etc.

Further, by controlling the concentration of the vitamin $B_6$ group in the culture medium used when assaying, the effective concentration of the test compound is decreased and the sensitivity of the assay system is improved. In the culture medium used in normal cell culture, pyridoxine, which is a member of the vitamin $B_6$ group, is present at about 5 to 20 µM, however, by selecting the concentration thereof lower than the above range, the sensitivity can be improved. In order to obtain the highest sensitivity, a culture medium from which the vitamin $B_6$ group is completely removed is used. By doing this, it also becomes possible to detect SPL inhibitory activity for compounds whose in vitro SPL inhibitory activity has not been found (such as THI) by conventional methods. By selecting an appropriate concentration of the vitamin $B_6$ group according to the derived species of the cultured cells to be used in the test, it becomes possible to evaluate the test compound under conditions closer to in vivo conditions. The culture medium to be used in the assay system of the present invention is preferably a culture medium containing the vitamin $B_6$ group at 1 µM or less, more preferably a culture medium containing the vitamin $B_6$ group at 100 nM or less. Even more preferably, the cells are washed with a culture medium, which does not contain any vitamin $B_6$ group, before the test compound is added and a culture medium which substantially does not contain any vitamin $B_6$ group is used in the assay.

The present assay method can be carried out using a multiwell plate such as a 96-well plate or a 384-well plate, and therefore can be automated easily. Accordingly, it becomes possible to select a compound which directly or indirectly inhibits SPL in cells by high-speed multiple sample screening.

As the test compound, a compound, a microbial metabolite, a plant or animal tissue extract, a derivative thereof, or a mixture thereof can be used. It is also possible to use a nucleic acid designed so that the expression level of SPL is decreased or a derivative thereof (such as an antisense oligonucleotide, a ribozyme, dsRNA or siRNA) as the test compound. The dose or concentration of the test compound may be appropriately set or a plurality of doses may be set by preparing, for example, a dilution series. The test compound can be administered in an appropriate state such as a solid or a liquid, and also the test compound may be dissolved in an appropriate buffer or a stabilizing agent or the like may be added thereto. In the method for screening of the present invention, cultured cells are used, and the test compound is used by being added to a culture medium. The test compound may be added to the culture medium from the initiation of the culture or in the course of the culture. The number of times that the test compound is added is not limited to one. The culture period in the presence of the test compound may also be appropriately set, but is preferably from 30 minutes to 2 weeks, more preferably from 2 hours to 72 hours, even more preferably from 5 hours to 24 hours. The time of treatment with the compound in the Examples is 5 hours, but is not limited thereto.

2. Assay Method and Support Material to be Used in the Present Invention

Several assay formats can be used for carrying out the method of the present invention, however, a preferred assay format is a scintillation assay such as a scintillation proximity assay (SPA). The SPA technique involves the use of scintillant beads containing an organic scintillant such as PPO. The assay is usually carried out in an aqueous buffer solution using a radioisotope such as $^3$H, $^{125}$I, $^{14}$C, $^{35}$S or $^{33}$P which emits low energy radiation, the energy of which is easily dissipated in an aqueous environment. For example, an electron emitted from $^3$H only has an average energy of 6 keV and has a very short path length in water. When a molecule labeled with one of these radioisotopes is bound to a bead surface directly or through an interaction with another molecule previously bound to the bead, the scintillant is activated by the emitted radiation to produce light. The amount of light produced is proportional to the number of labeled molecules bound to the beads and can be easily measured with a liquid scintillation (LS) counter. When the labeled molecule is not bound to the beads, its radiation energy is absorbed by the surrounding aqueous solvent before it reaches the bead and light is not produced. Accordingly, a ligand in a bound state gives a scintillation signal, but a ligand in a free state gives a very low background noise. Accordingly, it is not necessary to perform a separation step requiring a lot of time, which is a characteristic of conventional radioactive ligand binding assays. The procedure required in the assay is simplified to the step of a few easy pipetting operations, and therefore more favorable accuracy and reproducibility can be achieved and also higher throughput can be obtained.

In a more preferred embodiment, the method of the present invention includes binding a radiolabeled phosphorylated lipid (such as sphingosine-1-P) to SPA beads. The binding is preferably carried out through chemical or physical interaction with yttrium-silicate beads or yttrium-oxide beads, although other binding means can be contemplated. More specifically, the binding is achieved by the interaction (i.e. binding other than covalent binding) between the phosphate group of the phosphorylated substrate and the support surface. A labeled unphosphorylated lipid (such as $^3$H-Sph or $^3$H-dhSph) is phosphorylated by SPHKs and a labeled phosphorylated lipid (such as $^3$H-S1P or $^3$H-dhS1P) is generated. The generated phosphorylated lipid is usually promptly degraded by SPL, however, by adding a compound which inhibits the SPL activity, an increase in the amount of the labeled phosphorylated lipid is observed.

Next, the present specification will disclose a novel method for screening for a compound which inhibits the SPL activity using a specific support material. The support material has an ability to bind to a substrate for the SPL reaction such as a phosphorylated lipid, but does not have an ability to bind to a substrate such as an unphosphorylated lipid. Therefore, the amount of the lipid bound to the support shows a negative correlation with the SPL activity of the cultured cells. The support may contain a functional group (such as an antibody or another reactive group) capable of discriminating a phosphorylated lipid from an unphosphorylated lipid or may be composed of a substance having the ability to discriminate such lipids (or may contain such a substance).

The support may be composed, at least in part, of a silicate, polyvinyltoluene (PVT), (poly)acrylamide, agarose, sepharose, polystyrene, or the like. Specific examples of the support material include PVT or a silicate material, optionally coated with a ligand such as WGA, streptavidin or polylysine. More preferred materials include yttrium oxide or yttrium silicate (YtSi) (which is optionally coated or functionalized) or PVT.

In a more preferred embodiment, the support contains a scintillant (or an organic scintillant). The scintillant is preferably insoluble in water and can be excited to a higher energy level when the labeled lipid is bound to the support. The scintillant should produce sufficient light energy so as to be detected using a suitable device (such as a scintillation counter). A typical example of the scintillant is diphenyloxazole (PPO). This scintillant is efficiently excited by a radioisotope which emits a β-ray.

The support material suitable for use in the present invention can be found among commercially available products such as WGA-coated PVT beads (RPNQ0001), PEI-treated WGA PVT beads (RPNQ0003), streptavidin-coated PVT beads (RPNQ0007), polylysine-coated yttrium silicate beads (RPNQ0010), WGA-coated yttrium silicate beads (RPNQ0011), streptavidin-coated yttrium silicate beads (RPNQ0012), RNA-binding yttrium silicate SPA beads (RPNQ0013) and membrane-binding yttrium oxide SPA beads (RPNQ0280), all of which are products of PerkinElmer.

The labeled lipid to be used in the present invention is preferably radiolabeled. The radiolabeling can be carried out using any radioisotopes including $^3$H, $^{125}$I, $^{14}$C, $^{35}$S, $^{33}$P and $^{32}$P. The radioisotope is preferably a radioisotope which emits low energy radiation, the energy of which is easily dissipated in an aqueous environment. It is required that the unbound labeled substrate should essentially fail to activate the scintillant contained in the support material. The property of the isotope may also be selected depending on the type of scintillant. For example, when PPO is used as the scintillant, the isotope preferably emits a β-ray such as $^3$H.

The amount of labeled lipid to be used for the assay can be adjusted by those skilled in the art. In a typical experiment, 0.01 to 10 μM, preferably 0.02 to 1 μM of a lipid or 0.01 to 0.5 μCi of $^3$H-Sph or $^3$H-dhSph is used in each assay. In the Examples in this description, 0.05 μCi of the labeled substrate at a concentration of 1 μM is used, however, the radioactivity and concentration of the labeled lipid to be used in the assay are not particularly limited thereto. The number of cells to be used in the assay depends on the SPL activity of the cells, and can be adjusted by those skilled in the art.

3. Pharmaceutical Containing SPL Inhibitor

The compound found by the method for screening of the present invention or a pharmaceutically acceptable salt thereof has excellent S1P lyase inhibitory capacity, and therefore can suppress the activity of the immune system. Accordingly, the compound found by the method for screening of the present invention or a pharmaceutically acceptable salt thereof can be used for preventing or treating an inflammatory bowel disease (IBD) (such as ulcerative colitis or Crohn's disease), an autoimmune disease (such as rheumatoid arthritis, systemic lupus erythematosus, antiphospholipid antibody syndrome, multiple myositis, dermatomyositis, systemic scleroderma, Sjogren's syndrome, polyarteritis nodosa, microscopic polyarteritis, allergic granulomatous angiitis, Wegener's granulomatosis, or a mixed connective tissue disease), multiple sclerosis (MS) and an allergic disease (such as atopic dermatitis, allergic rhinitis (pollinosis), allergic conjunctivitis, allergic gastroenteritis, bronchial asthma, infantile asthma, food allergy, drug allergy or urticaria), or can be used as an active ingredient of a pharmaceutical composition for suppressing rejection response against transplant.

A pharmaceutical composition containing, as an active ingredient, the compound found by the method for screening of the present invention or a pharmaceutically acceptable salt thereof may be administered systemically or locally, and orally or parenterally when administered to a mammal (e.g., a human, horse, cow, pig, etc., preferably a human).

The pharmaceutical composition of the present invention can be prepared according to various preparation methods of formulations which are usually employed by selecting an appropriate form depending on the administration method.

Examples of the form of the pharmaceutical composition for oral administration include tablets, pills, powders, granules, capsules, solutions, suspensions, emulsions, syrups, elixirs, and the like. For preparation of the pharmaceutical composition in such a form, excipients, binders, disintegrants, lubricants, swelling agents, swelling adjuvants, coating agents, plasticizers, stabilizers, antiseptics, antioxidants, colorants, dissolution aids, suspending agents, emulsifiers, sweeteners, preservatives, buffers, diluents, wetting agents, and the like which are usually employed as additives may be appropriately selected as needed, to allow the pharmaceutical composition to be produced according to ordinary methods.

Examples of the form of the pharmaceutical composition for parenteral administration include injection solutions, ointments, gels, creams, poultices, patches, nebulas, inhalants, sprays, eye drops, nose drops, suppositories, inhalants, and the like. For preparation of the pharmaceutical composition in such a form, stabilizing agents, antiseptics, dissolution aids, humectants, preservatives, antioxidants, flavoring agents, gelling agents, neutralizers, dissolution aids, buffers, isotonic agents, surfactants, colorants, buffering agents, thickeners, wetting agents, fillers, absorption promoters, suspending agents, binders, and the like which are usually employed as additives may be appropriately selected as needed, to allow the pharmaceutical composition to be produced according to ordinary methods.

While the dosage of the compound found by the method for screening of the present invention or a pharmaceutically acceptable salt thereof varies depending on symptoms, age, body weight, or the like, in the case of oral administration, the dosage is 1 to 2000 mg, preferably 1 to 400 mg, in terms of the amount of the compound, per dose once to several times a day for an adult, and in the case of parenteral administration, the dosage is 0.01 to 500 mg, preferably 0.1 to 300 mg, in terms of the amount of the compound, per dose once to several times a day for an adult.

EXAMPLES

Hereinafter, the present invention will be described more specifically with reference to Examples, however, the present invention is not limited thereto.

Example 1

Detection of $^3$H-dhS1P by SPA $^3$H-dhS1P (60 Ci/mmol, American Radiolabeled Chemicals, ART 0618) or $^3$H-dhSph (60 Ci/mmol, American Radiolabeled Chemicals, ART 0460) was serially diluted with a cell lysis buffer (a mixed solution of IP-One Tb conjugate & lysis buffer and IP1 stimulation buffer (1×) (3:7) which are components of IP-One Tb Kit, manufactured by Cisbio, Inc.).

In order to examine the total radioactivity, 50 µL of each of the diluted solutions of the above $^3$H-labeled compounds was mixed with 5 mL of a liquid scintillator (Hionic-Fluor, PerkinElmer), and the radioactivity thereof was measured using a liquid scintillation counter (Aloka).

In order to examine the efficiency of a conventional separation extraction method, to 50 µmL of each of the diluted solutions of the above $^3$H-labeled compounds, 50 µL of a 0.2 M sodium hydroxide solution and 100 µL of a mixed solution of chloroform and methanol (chloroform: methanol=2:1) were added, and the resulting mixture was vigorously stirred and then centrifuged at room temperature for 3 minutes at 8,400 g. A 70 µL portion of the resulting aqueous layer was taken and mixed with 5 mL of the liquid scintillator, and the radioactivity thereof was measured using a liquid scintillation counter.

In order to examine the efficiency of detection of $^3$H-dhS1P by SPA, RNA Binding YSi SPA Scintillation Beads (SPA beads, PerkinElmer, RPNQ0013) were diluted to 8 times such that glycerol was contained at 50% in the final concentration. After the diluted beads were dispensed into a white 96-well plate (OptiPlate-96 (white, 96-well), PerkinElmer) at 20 µL/well, 50 µL of each of the diluted solutions of the above $^3$H-labeled compounds was added thereto and mixed therewith. Then, the plate was covered with a transparent plate seal (TopSeal-A, PerkinElmer) and left overnight at room temperature under shading. On the next day, the radioactivity thereof was measured using a microplate scintillation counter (TopCount NXT, PerkinElmer).

Figure 2:
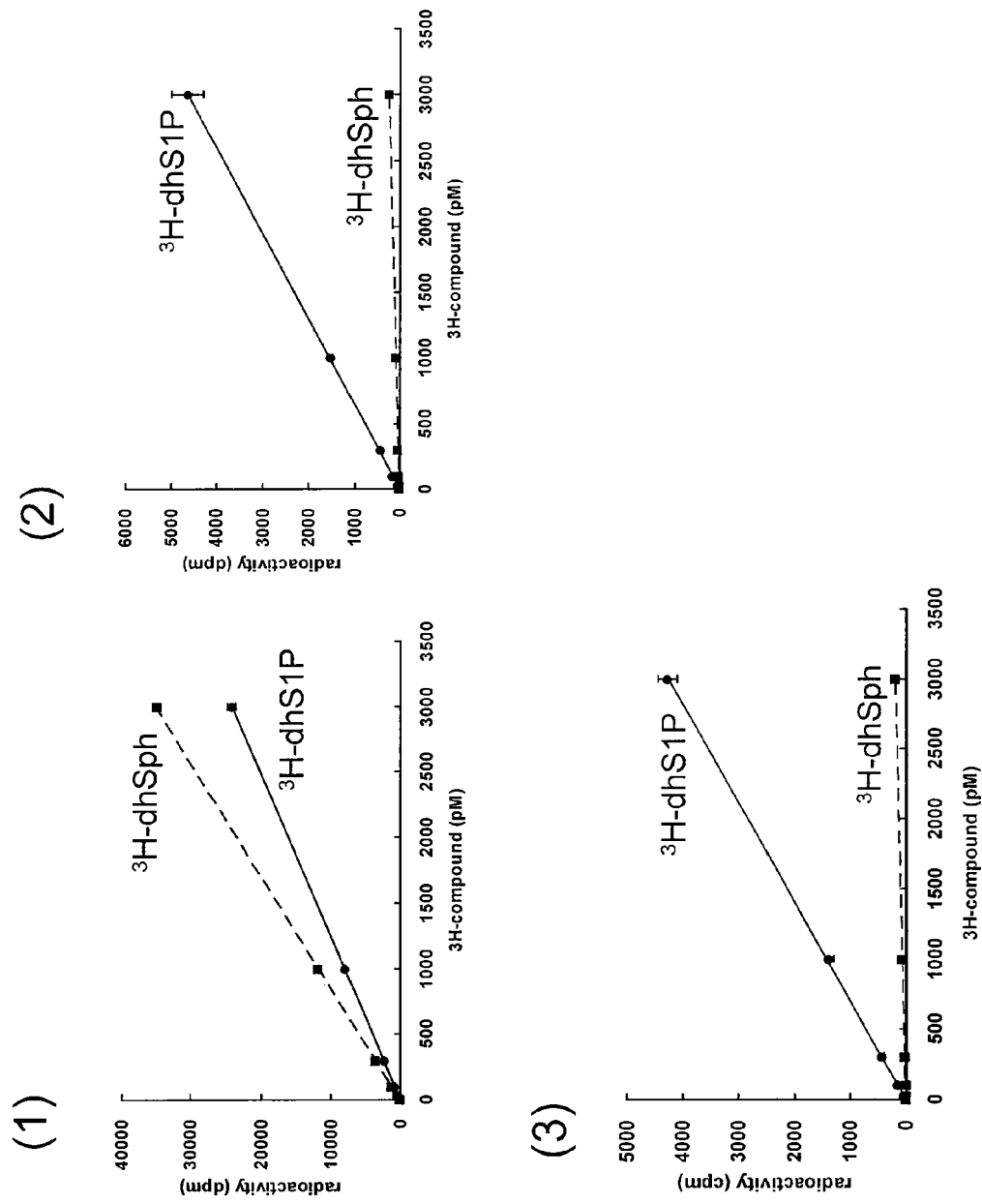
FIG. 2 shows graphs indicating that $^3$H-dhS1P can be selectively detected by SPA with an efficiency equivalent to that of a conventional alkaline chloroform extraction method.

The results are shown in FIG. 2. By SPA, $^3$H-dhS1P could be selectively detected with an efficiency equivalent to that of a conventional alkaline chloroform extraction method.

Example 2

Confirmation of Various Effects of siRNA Transfection

1) Cell Culture and Culture Media

A mouse thymic epithelial cell line (IT-79MTNC3 cells, The Cell Bank Division of Japan Health Sciences Foundation) was cultured using Dulbecco's Modified Eagle Medium (DMEM, Invitrogen) containing 10% fetal bovine serum (FBS) (DMEM-10% FBS) at 37° C. in the presence of 5% $CO_2$. When the cells were used for transfection or assay, the cells were detached with 0.05% trypsin-EDTA (Invitrogen), followed by centrifugation, thereby collecting the cells. When the cells were treated with a compound or used for incorporating $^3$H-dhSph, DMEM containing 0.1% bovine serum albumin (BSA, Sigma) (DMEM-0.1% BSA) or vitamin $B_6$ group-depleted Dulbecco's Modified Eagle Medium (VB$_6$-free DMEM, Cell Science & Technology Institute, Inc.) containing 0.1% BSA (VB$_6$-free DMEM-0.1% BSA) was used.

2) siRNA Transfection

To IT-79MTNC3 cells prepared at 1×10$^6$ cells/100 µL with Nucleofector Solution L (Lonza), 200 pmol of one of three siRNAs with different sequences (Silencer select Pre-designed siRNA, Ambion, s73643 to s73645) targeted against mouse SPL or a negative control siRNA (QIAGEN) was added, and the cells were transfected by a program T-030 using Nucleofector II (Amaxa).

3) Gene Expression Analysis by Real-Time PCR

In order to examine knockdown efficiency, the transfected cells were suspended in DMEM-10% FBS, and seeded in a 6-well plate for cell culture (Sumitomo Bakelite Co., Ltd.) at 2×10$^5$ cells/well, and then cultured at 37° C. in the presence of 5% $CO_2$ for 24 hours or 48 hours. After the culture, the total RNA was extracted from the IT-79MTNC3 cells using an RNA extraction kit (RNeasy Mini Kit, QIAGEN), and further, a cDNA was prepared using PrimeScript 1st strand cDNA Synthesis Kit (TaKaRa Bio, Inc.). By using the prepared cDNA as a template and also using QuantiTect SYBR Green PCR Kit (QIAGEN) and primers (Perfect Real Time Primer, TaKaRa Bio, Inc.) specific to a mouse glyceraldehyde-3-phosphate dehydrogenase (GAPDH) gene or a mouse SPL gene, a relative quantitative analysis of SPL mRNA in each sample was carried out by a real-time PCR system (Mx4000 Multiplex Quantitative PCR System, Stratagene). The results were calculated as a ratio of the expression level of SPL mRNA in the cells transfected with the negative control siRNA.

4) Measurement of SPL Activity in Lysate of Cells Transfected with siRNA

In order to prepare a lysate of SPL gene-knockdown IT-79MTNC3 cells, the transfected cells were suspended in DMEM-10% FBS and seeded in a 12-well plate for cell culture (Sumitomo Bakelite Co., Ltd.) at $1.5 \times 10^5$ cells/well, and then cultured at 37° C. in the presence of 5% $CO_2$ for 24 hours or 48 hours. After the culture, the IT-79MTNC3 cells were collected, and 120 µL, of a homogenization buffer (50 mM HEPES-NaOH (pH=7.4), 0.15 M NaCl, 10% Glycerol, 1 mM EDTA, 1 mM DTT, Complete protease inhibitor cocktail (Roche)) was added thereto. The resulting mixture was subjected to an ultrasonic treatment using a sonicator (HandySonic, Tomy Seiko Co., Ltd.), followed by centrifugation at 4° C. for 3 minutes at 1,000 g, and the resulting supernatant was used as a cell lysate. The quantitative determination of protein by the Bradford method was carried out using a portion of the cell lysate.

In order to measure the SPL activity in the cell lysate, the cell lysate was diluted to 0.6 mg protein/mL with a homogenization buffer, and the diluted solution was mixed with $^3$H-dhS1P (3.4 nM) as a substrate and a reaction buffer (a 0.1 M potassium phosphate solution (pH=7.4), 25 mM NaF, 5 mM $Na_3VO_4$, 1 mM EDTA, 1 mM DTT, 0.1% Triton X-100, 2 µM cold dhS1P) to make the final volume 50 µL. Then, the reaction was allowed to proceed at 37° C. for 1 hour. A sample in which the reaction was allowed to proceed on ice for 1 hour was used as a negative control. After the reaction, 50 µL of a 0.2 M sodium hydroxide solution and 100 µL, of a mixed solution of chloroform and methanol (chloroform:methanol=2:1) were added thereto, and the resulting mixture was vigorously stirred and then centrifuged at room temperature for 3 minutes at 8,400 g. A 30 µL portion of the resulting organic layer was taken and mixed with 5 mL of the liquid scintillator, and the radioactivity thereof was measured using a liquid scintillation counter. The obtained count was assumed to reflect the amount of degradation products by the SPL reaction, and the results were calculated as a ratio of the SPL activity of the cells transfected with the negative control siRNA.

5) SPA in Cells Transfected with siRNA

In order to detect the accumulation of $^3$H-dhS1P in the SPL gene-knockdown IT-79MTNC3 cells by SPA, the transfected cells were suspended in DMEM-10% FBS containing 25 µM fumonisin B1 (Enzo Life Sciences), and seeded in a 96-well plate for cell culture (Sumitomo Bakelite Co., Ltd.) at $1 \times 10^4$ cells/well, and then cultured at 37° C. in the presence of 5% $CO_2$ for 24 hours or 48 hours. The culture supernatant was first removed, and then, 50 µL of DMEM-0.1% BSA containing 8.3 nM $^3$H-dhSph and 1 µM dhSph (Enzo Life Sciences) was added thereto, and the cells were cultured at 37° C. in the presence of 5% $CO_2$ for 30 minutes. After the culture supernatant was removed, 70 µL of a cell lysis buffer was added thereto, and the resulting mixture was left at room temperature for 2 hours. A 50 µL portion of the resulting cell lysate was mixed with SPA beads (obtained by being diluted to 8 times such that glycerol was contained at 50% in the final concentration), which had previously been dispensed into a white 96-well plate at 20 µL/well. Then, the plate was covered with a transparent plate seal and left overnight at room temperature under shading. On the next day, the radioactivity thereof was measured using a microplate scintillation counter.

Figure 3:
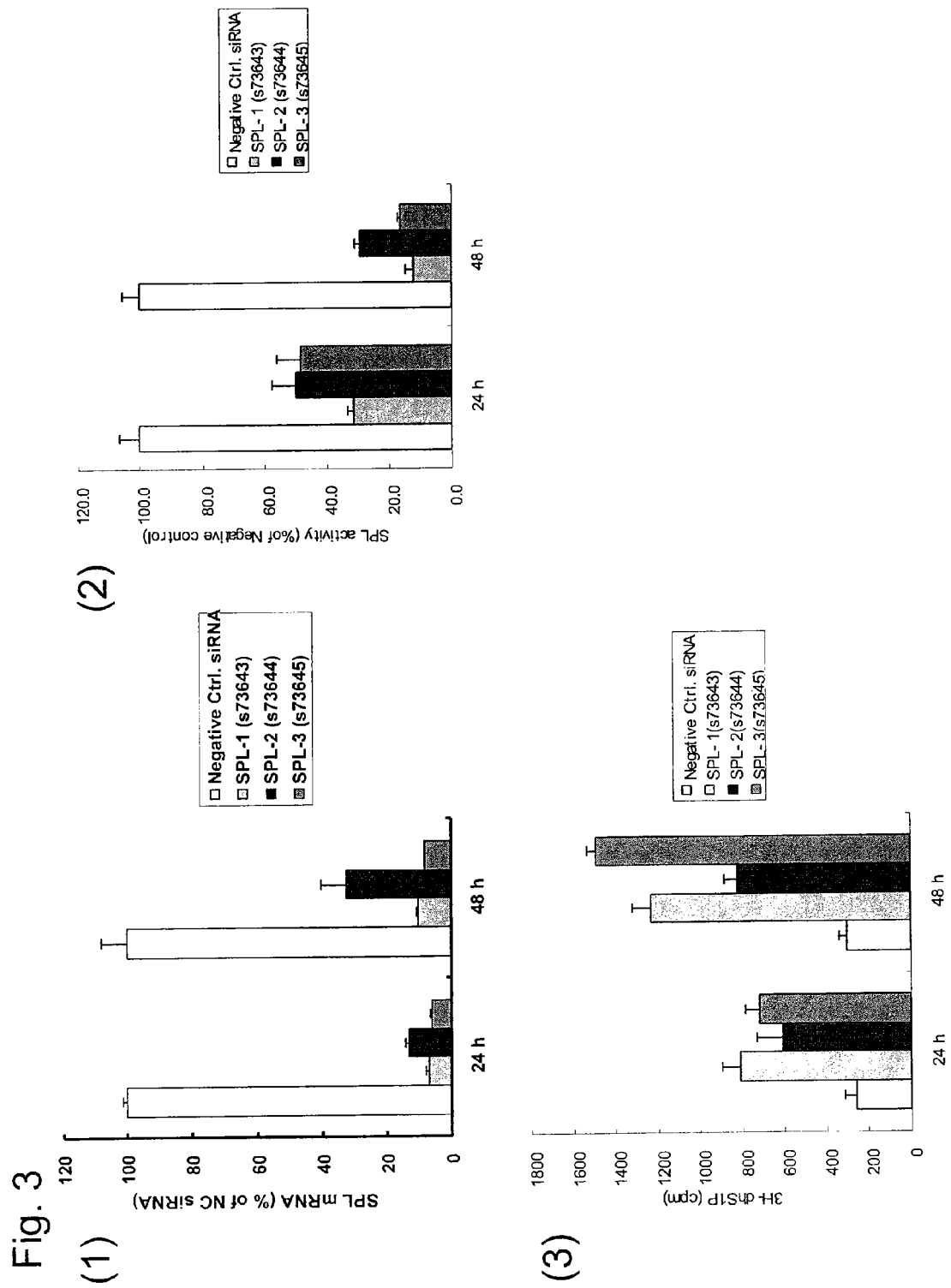
FIG. 3 shows graphs indicating various effects of siRNA transfection on IT-79MTNC3 cells.

The results are shown in FIG. 3. By siRNA transfection, the expression level of SPL mRNA was suppressed by 86% or more after 24 hours and by 67% or more after 48 hours. In addition, a decrease in SPL activity in the lysate corresponding thereto could also be confirmed. Further, by the constructed SPA, the accumulation of intracellular $^3$H-dhS1P could be detected.

Example 3

Measurement of SPL Activity Using Known Inhibitor

1) SPA Using Known SPL Inhibitor

In order to evaluate the activity of a test compound for accumulating $^3$H-dhS1P, IT-79MTNC3 cells were suspended in DMEM-10% FBS containing 25 µM fumonisin B1, and seeded in a 96-well plate for cell culture at $1 \times 10^4$ cells/well, and then cultured at 37° C. in the presence of 5% $CO_2$ for a whole day and night. On the next day, the culture supernatant was first removed, and then, 40 µL of DMEM-0.1% BSA (or $VB_6$-free DMEM-0.1% BSA) containing a serially diluted test compound was added thereto, and the cells were cultured at 37° C. in the presence of 5% $CO_2$ for 4.5 hours. Thereafter, 10 µL of DMEM-0.1% BSA (or $VB_6$-free DMEM-0.1% BSA) containing 83 nM $^3$H-dhSph and 5 µM dhSph was added thereto, and the cells were cultured at 37° C. in the presence of 5% $CO_2$ for 30 minutes. After the culture supernatant was removed, 70 µL of a cell lysis buffer was added thereto, and the resulting mixture was left at room temperature for 2 hours. A 50 µL portion of the resulting cell lysate was mixed with SPA beads (obtained by being diluted to 8 times such that glycerol was contained at 50% in the final concentration), which were previously dispensed into a white 96-well plate at 20 µL/well. Then, the plate was covered with a transparent plate seal and left overnight at room temperature under shading. On the next day, the radioactivity thereof was measured using a microplate scintillation counter. In the case of using $VB_6$-free DMEM, before the culture medium containing the test compound was added, washing was carried out twice with 150 µL of $VB_6$-free DMEM-0.1% BSA, thereby preventing the carryover of the vitamin $B_6$ group contained in DMEM used when seeding.

2) Measurement of Intracellular S1P by LC-MS

In order to evaluate the activity of a test compound for accumulating S1P, IT-79MTNC3 cells were suspended in DMEM-10% FBS containing 25 µM fumonisin B1, and seeded in a 24-well plate for cell culture at $5 \times 10^4$ cells/well, and then cultured at 37° C. in the presence of 5% $CO_2$ for a whole day and night. On the next day, the culture supernatant was first removed, and then, 450 µL of DMEM-0.1% BSA (or $VB_6$-free DMEM-0.1% BSA) containing a serially diluted test compound was added thereto, and the cells were cultured at 37° C. in the presence of 5% $CO_2$ for 4.5 hours. Thereafter, 50 µL of DMEM-0.1% BSA (or $VB_6$-free DMEM-0.1% BSA) containing 10 µM Sph (Enzo Life Sciences) was added thereto, and the cells were cultured at 37° C. in the presence of 5% $CO_2$ for 30 minutes. After the culture supernatant was removed, the cells were washed with PBS and collected. Then, 150 µL of a mixed solution of acetonitrile and 1 M hydrochloric acid (acetonitrile:hydrochloric acid=4:1) was added to the cells, and the resulting mixture was subjected to an ultrasonic treatment using a sonicator. The amount of S1P was measured by LC-MS by Mitsubishi Chemical Medience Corporation. In the case of using $VB_6$-free DMEM, before the culture medium containing the test compound was added, washing was carried out twice with 600 µL of $VB_6$-free DMEM-0.1% BSA, thereby preventing the carryover of the vitamin $B_6$ group contained in DMEM used when seeding.

3) Measurement of SPL Activity in Lysate of Cells Treated with Compound

In order to prepare a lysate of cells treated with a test compound, IT-79MTNC3 cells were suspended in DMEM-10% FBS containing 25 µM fumonisin B1 and seeded in a 12-well plate for cell culture at $1×10^5$ cells/well, and then cultured at 37° C. in the presence of 5% $CO_2$ for a whole day and night. On the next day, the culture supernatant was first removed, and then, 500 µL of DMEM-0.1% BSA (or $VB_6$-free DMEM-0.1% BSA) containing a serially diluted test compound was added thereto, and the cells were cultured at 37° C. in the presence of 5% $CO_2$ for 4.5 hours. Thereafter, 55 µL of DMEM-0.1% BSA (or $VB_6$-free DMEM-0.1% BSA) containing 10 µM dhSph was added thereto, and the cells were cultured at 37° C. in the presence of 5% $CO_2$ for 30 minutes. After washing the IT-79MTNC3 cells with PBS, the cells were collected. Then, 150 µL of a homogenization buffer was added to the cells, and the resulting mixture was subjected to an ultrasonic treatment using a sonicator, followed by centrifugation at 4° C. for 3 minutes at 1,000 g, and the resulting supernatant was used as a cell lysate. The quantitative determination of protein by the Bradford method was carried out using a portion of the cell lysate. In the case of using $VB_6$-free DMEM, before the culture medium containing the test compound was added, washing was carried out twice with 1 mL of $VB_6$-free DMEM-0.1% BSA, thereby preventing the carryover of the vitamin $B_6$ group contained in DMEM used when seeding.

In order to measure the SPL activity in the lysate prepared using the cells treated with the compound, the cell lysate was diluted to 1 mg protein/mL with a homogenization buffer, and the diluted solution was mixed with $^3$H-dhS1P (3.4 nM) as a substrate and a reaction buffer (a 0.1 M potassium phosphate solution (pH-7.4), 25 mM NaF, 5 mM $Na_3VO_4$, 1 mM EDTA, 1 mM DTT, 0.1% Triton X-100, 2 µM cold dhS1P) to make the final volume 50 µL. Then, the reaction was allowed to proceed at 37° C. for 1 hour. A sample in which the reaction was allowed to proceed on ice for 1 hour was used as a negative control. After the reaction, 50 µL of a 0.2 M sodium hydroxide solution and 100 µL of a mixed solution of chloroform and methanol (chloroform:methanol=2:1) were added thereto, and the resulting mixture was vigorously stirred and then centrifuged at room temperature for 3 minutes at 8,400 g. A 30 µL portion of the resulting organic layer was taken and mixed with 5 mL of the liquid scintillator, and the radioactivity thereof was measured using a liquid scintillation counter. The obtained count was assumed to reflect the amount of degradation products by the SPL reaction, and the SPL activity of each sample was calculated as a ratio of that in the group without treatment with the compound.

Figure 4:
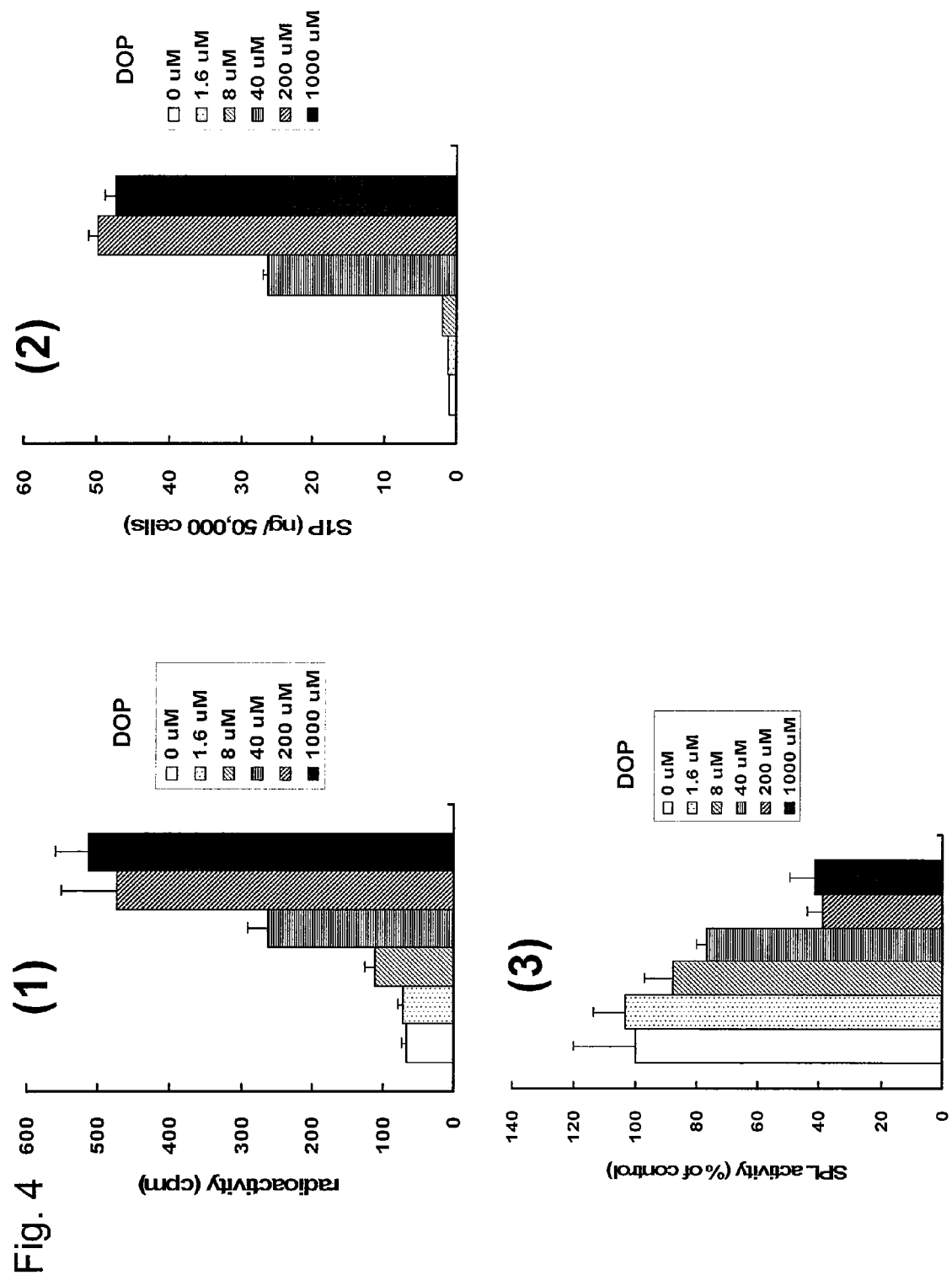
FIG. 4 shows graphs indicating the SPL inhibitory activity of 4-deoxypyridoxine (DOP) in IT-79MTNC3 cells under normal conditions.

FIG. 4 shows the respective assay results under normal conditions. 4-Deoxypyridoxine (DOP) which is a non-specific SPL inhibitor showed concentration-dependent response by SPA. In the same manner, also with respect to the amount of intracellular S1P and the SPL activity in the lysate, the activity of DOP was detected in substantially the same concentration range.

Figure 5:
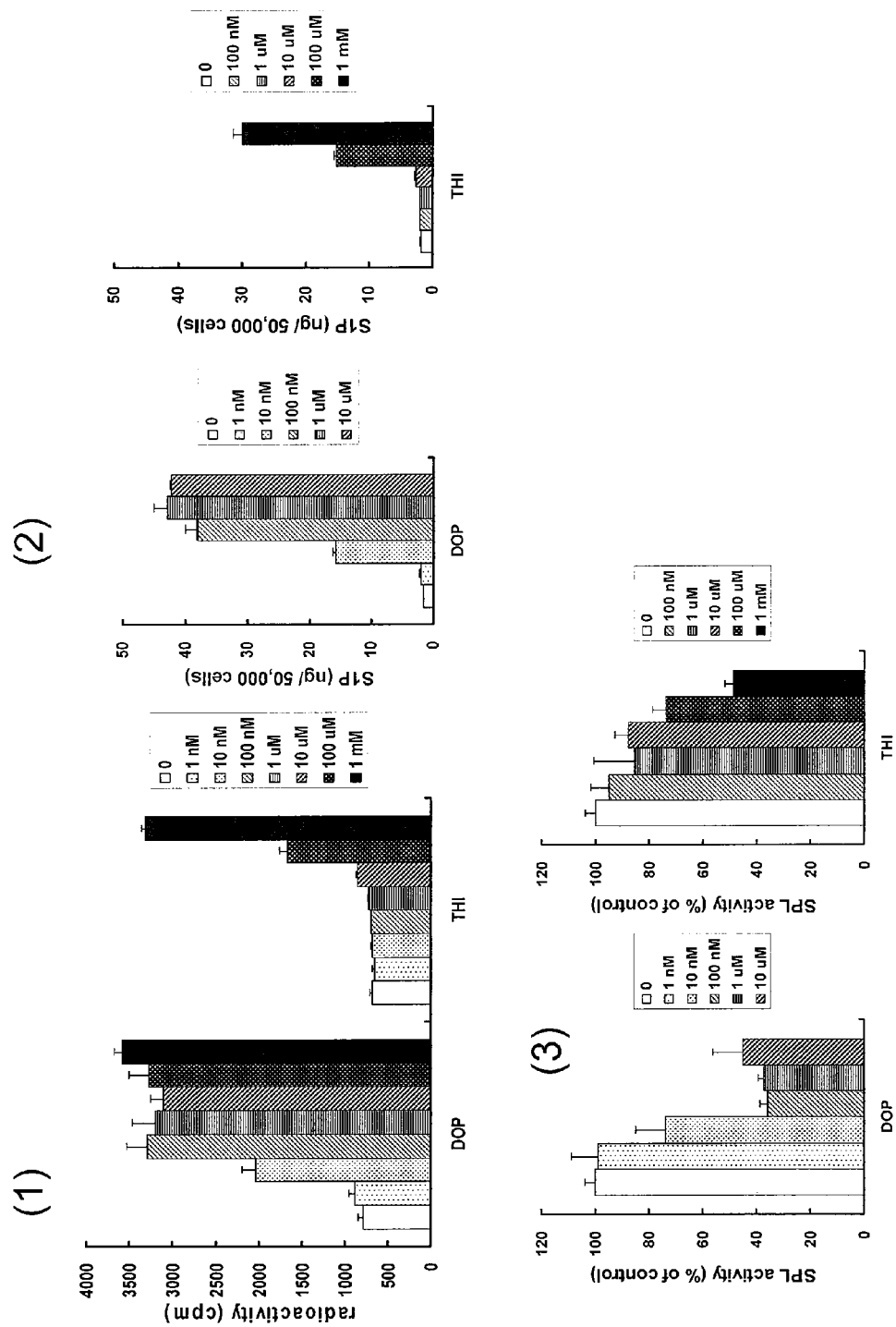
FIG. 5 shows graphs indicating SPL inhibitory activity of 4-deoxypyridoxine or 2-acetyl-4-tetrahydroxybutylimidazole (THI) in IT-79MTNC3 cells under vitamin $B_6$ group-depleted conditions.

FIG. 5 shows the respective assay results under the conditions of using $VB_6$-free DMEM. The effective concentration of 4-deoxypyridoxine (DOP) which is a non-specific SPL inhibitor in SPA was significantly decreased as compared with the case where normal DMEM was used. Further, in the case of THI, its concentration-dependent activity was detected. These test compounds also exhibited their activity in substantially the same concentration range with respect to the amount of intracellular S1P and the SPL activity in the lysate.

Further, the effect of the vitamin $B_6$ group on the activity of inhibiting the SPL activity was separately confirmed. As a result, in the case of using normal DMEM (containing about 20 µM pyridoxine), the EC50 of DOP was 46 µM. Further, the EC50 of DOP in the presence of 1 µM pyridoxine was 1.6 µM, and the EC50 of DOP in the presence of 100 nM pyridoxine was 27 nM. Further, in the case of THI, when using normal DMEM or in the presence 1 µM pyridoxine, an inhibitory activity against the SPL activity could not be observed. However, in the presence of 100 nM pyridoxine, the EC50 of THI was about 250 µM, and the SPL inhibitory activity could be observed. In this manner, by decreasing the concentration of the vitamin $B_6$ group lower than that of a culture medium used for normal cell culture, the sensitivity of the measurement of SPL inhibitory activity could be improved.

Example 4

Examination of Effect of Treatment with Fumonisin B1

In order to examine the improving effect of a treatment with fumonisin B1 on a signal/background ratio, IT-79MTNC3 cells were suspended in DMEM-10% FBS containing 0 or 25 µM fumonisin B1, and seeded in a 96-well plate for cell culture at $1×10^4$ cells/well, and then cultured at 37° C. in the presence of 5% $CO_2$ for a whole day and night. On the next day, the culture supernatant was first removed, and then 40 µL of DMEM-0.1% BSA containing DOP (or not containing DOP) was added thereto, and the cells were cultured at 37° C. in the presence of 5% $CO_2$ for 4.5 hours. Thereafter, 10 µL of DMEM-0.1% BSA containing 42 nM $^3$H-dhSph and 5 µM dhSph was added thereto, and the cells were cultured at 37° C. in the presence of 5% $CO_2$ for 30 minutes. After the culture supernatant was removed, 70 µL of a cell lysis buffer was added thereto, and the resulting mixture was left at room temperature for 2 hours. A 50 µL portion of the resulting cell lysate was mixed with SPA beads (obtained by being diluted to 8 times such that glycerol was contained at 50% in the final concentration), which were previously dispensed into a white 96-well plate at 20 µL/well. Then, the plate was covered with a transparent plate seal and left overnight at room temperature under shading. On the next day, the radioactivity thereof was measured using a microplate scintillation counter.

Figure 6:
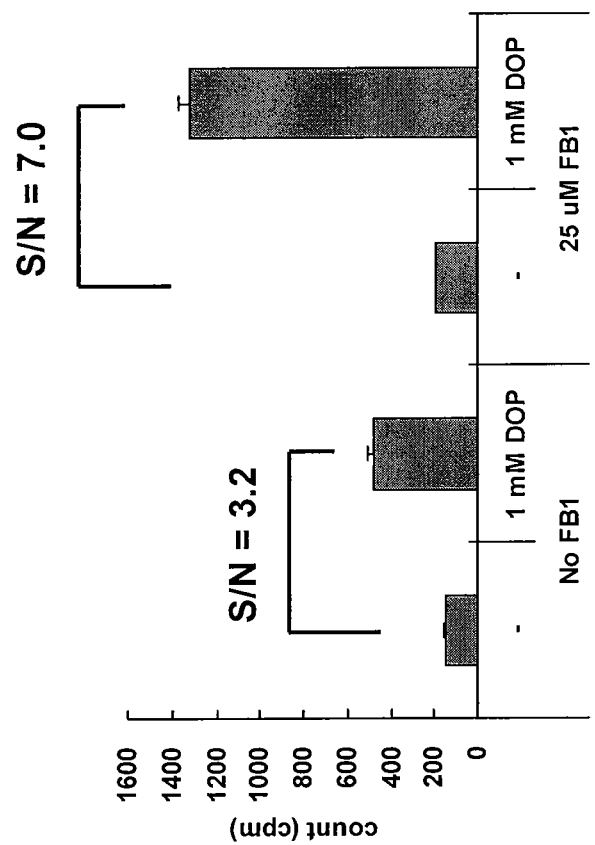
FIG. 6 shows a graph indicating that the signal/background ratio in detection of SPL inhibitory activity (the accumulation of $^3$H-dhS1P in cells) of 4-deoxypyridoxine is improved by the addition of fumonisin B1 (FB1).

The results are shown in FIG. 6. By performing a treatment with fumonisin B1 in advance, it was possible to improve the signal/background ratio of the assay.

INDUSTRIAL APPLICABILITY

By the method for screening of the present invention, it becomes possible to find a compound which exhibits an immunosuppressive activity due to an SPL inhibitory activity rapidly, simply and highly sensitively.

The invention claimed is:
1. A method for identifying, selecting or testing a compound which inhibits the activity of sphingosine-1-phosphate lyase, comprising:

(i) seeding cells which express sphingosine-1-phosphate lyase and culturing the cells;

(ii) mixing the cells with a labeled lipid substrate and a test compound and culturing the cells, wherein in step (i), step (ii), or both steps (i) and (ii), the cells are cultured using a culture medium containing vitamin $B_6$ group wherein the concentration of the vitamin $B_6$ group is 20 µM or less;

(iii) lysing the cells or separating the culture supernatant from the cells;

(iv) contacting a support material which binds to a phosphorylated lipid with the lysed cells or the culture supernatant;

(v) measuring the amount of labeled phosphorylated lipid bound to the support material; and (vi) determining whether the activity of sphingosine-1-phosphate lyase is inhibited wherein an increase in the amount of the labeled phosphorylated lipid compared with the case in which the test compound is not added indicates inhibition of sphingosine-1-phosphate lyase.

2. The method of claim 1, wherein the lipid substrate is sphingosine or dihydrosphingosine.

3. The method of claim 1, wherein the concentration of the vitamin $B_6$ group is 1 µM or less.

4. The method of claim 1, wherein the concentration of the vitamin $B_6$ group is 100 nM or less.

5. The method of claim 1, wherein the cells are washed with a culture medium which does not contain the vitamin $B_6$ group before the test compound is added, and in step (ii), the culture medium does not contain the vitamin $B_6$ group.

6. The method of claim 1, wherein the support material comprises scintillation proximity assay (SPA) beads.

7. The method of claim 6, wherein the SPA beads are RNA-binding yttrium silicate SPA beads.

8. The method of claim 1, wherein in step (i), step (ii), or both steps (i) and (ii), a ceramide synthase inhibitor is added.

9. The method of claim 8, wherein the ceramide synthase inhibitor is fumonisin B1.

10. The method of claim 1, wherein the compound treats an inflammatory bowel disease, an autoimmune disease, multiple sclerosis or an allergic disease.

11. The method of claim 10, wherein the inflammatory bowel disease is ulcerative colitis or Crohn's disease.

12. The method of claim 10, wherein the autoimmune disease is rheumatoid arthritis, systemic lupus erythematosus, antiphospholipid antibody syndrome, multiple myositis, dermatomyositis, systemic scleroderma, Sjogren's syndrome, polyarteritis nodosa, microscopic polyarteritis, allergic granulomatous angiitis, Wegener's granulomatosis or a mixed connective tissue disease.

13. The method of claim 10, wherein the allergic disease is atopic dermatitis, allergic rhinitis, pollinosis, allergic conjunctivitis, allergic gastroenteritis, bronchial asthma, infantile asthma, food allergy, drug allergy or urticaria.

\* \* \* \* \*